(12) United States Patent
Claar et al.

(10) Patent No.: US 10,926,029 B2
(45) Date of Patent: Feb. 23, 2021

(54) IV MEMBRANE ATTACHMENT SYSTEMS AND METHODS

(71) Applicant: Becton, Dickinson and Company, Franklin Lakes, NJ (US)

(72) Inventors: Steven Claar, Draper, UT (US); Kohorneh A. Mallay, Sandy, UT (US); Brent R. Stoddard, Roy, UT (US); Shaun Staley, Murray, UT (US); Justin G. Hortin, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/239,304

(22) Filed: Jan. 3, 2019

(65) Prior Publication Data

US 2019/0151534 A1 May 23, 2019

Related U.S. Application Data

(62) Division of application No. 15/078,722, filed on Mar. 23, 2016, now Pat. No. 10,201,667.

(Continued)

(51) Int. Cl.
*A61M 5/165* (2006.01)
*A61M 5/14* (2006.01)
(Continued)

(52) U.S. Cl.
CPC .......... *A61M 5/165* (2013.01); *A61M 5/1411* (2013.01); *A61M 5/38* (2013.01);
(Continued)

(58) Field of Classification Search
CPC ...... A61M 5/1411; A61M 5/162; A61M 5/36; A61M 5/1409; A61M 1/3627;
(Continued)

(56) References Cited

U.S. PATENT DOCUMENTS

| 2,129,983 A | 9/1938 | Bacon |
| 2,729,212 A | 1/1956 | Butler |

(Continued)

FOREIGN PATENT DOCUMENTS

| AU | 771431 B2 | 3/2004 |
| CA | 2 460 251 A1 | 4/2003 |

(Continued)

OTHER PUBLICATIONS

Braun, Product Detail, the URL retrieved from http://www.bbraunoem-industrial.com/products/ details.cfm?prodid=B0843225&id-Caps &area=C, p. 1 (Apr. 12, 2005).

(Continued)

*Primary Examiner* — Manuel A Mendez
(74) *Attorney, Agent, or Firm* — Kirton & McConkie; Craig Metcalf; Kevin Stinger

(57) ABSTRACT

An intravenous delivery system may have a liquid source containing a liquid, tubing, and an anti-run-dry membrane positioned such that the liquid, flowing form the liquid source to the tubing, passes through the anti-run-dry membrane. The anti-run-dry membrane may be positioned within an exterior wall of a drip unit, and may be secured to a seat of the exterior wall by an attachment component. The attachment component may have various forms, such as a secondary exterior wall that cooperates with the exterior wall to define a drip chamber, a washer positioned such that the anti-run-dry membrane is between the washer and the seat, and an adhesive ring formed of a pressure sensitive adhesive and secured to the anti-run-dry membrane and the seat via compression. Interference features may protrude inward from the exterior wall or outward from the anti-run-dry membrane to help keep the anti-run-dry membrane in place.

7 Claims, 6 Drawing Sheets

Related U.S. Application Data

(60) Provisional application No. 62/138,718, filed on Mar. 26, 2015.

(51) Int. Cl.
| | | |
|---|---|---|
| *A61M 5/38* | (2006.01) | |
| *B29C 45/14* | (2006.01) | |
| *B29C 65/08* | (2006.01) | |
| *B29C 65/48* | (2006.01) | |
| *B29C 65/70* | (2006.01) | |
| *B29C 70/68* | (2006.01) | |
| *B29L 23/00* | (2006.01) | |
| *B29C 65/16* | (2006.01) | |
| *B29C 65/00* | (2006.01) | |
| *B29K 105/20* | (2006.01) | |
| *B29K 681/00* | (2006.01) | |
| *B29L 31/00* | (2006.01) | |

(52) U.S. Cl.
CPC ........ *B29C 45/14065* (2013.01); *B29C 65/08* (2013.01); *B29C 65/4825* (2013.01); *B29C 65/70* (2013.01); *B29C 70/68* (2013.01); *A61M 2005/1657* (2013.01); *A61M 2205/7527* (2013.01); *A61M 2207/00* (2013.01); *B29C 65/16* (2013.01); *B29C 65/4895* (2013.01); *B29C 66/1122* (2013.01); *B29C 66/30221* (2013.01); *B29C 66/5326* (2013.01); *B29C 66/5344* (2013.01); *B29C 66/5346* (2013.01); *B29C 66/53241* (2013.01); *B29C 66/53421* (2013.01); *B29C 66/612* (2013.01); *B29C 66/71* (2013.01); *B29C 66/712* (2013.01); *B29C 66/73171* (2013.01); *B29K 2105/20* (2013.01); *B29K 2681/06* (2013.01); *B29L 2023/007* (2013.01); *B29L 2031/753* (2013.01)

(58) Field of Classification Search
CPC .... A61M 5/165; A61M 39/26; A61M 5/1408; A61M 5/38; A61M 5/14224; A61M 39/10; A61M 1/3621; A61M 5/142; A61M 39/1011; A61J 1/2096; A61J 1/2089

See application file for complete search history.

(56) References Cited

U.S. PATENT DOCUMENTS

| | | | |
|---|---|---|---|
| 2,954,028 A | 9/1960 | Smith | |
| 3,030,954 A | 4/1962 | Thornton, Jr. | |
| 3,390,677 A | 7/1968 | Razimbaud | |
| 3,520,416 A | 7/1970 | Keedwell | |
| 3,557,786 A | 1/1971 | Barr, Sr. et al. | |
| 3,631,654 A | 1/1972 | Riely et al. | |
| 3,722,697 A * | 3/1973 | Burke | B29C 65/08 210/451 |
| 3,744,492 A | 7/1973 | Leibinsohn | |
| 3,756,233 A | 9/1973 | Goldowsky | |
| 3,782,083 A * | 1/1974 | Rosenberg | B01D 46/10 55/491 |
| 3,806,386 A | 4/1974 | Burke et al. | |
| 3,931,818 A | 1/1976 | Goldowsky | |
| 3,960,149 A | 6/1976 | Bujan | |
| 4,013,072 A * | 3/1977 | Jess | A61M 5/165 604/252 |
| 4,034,754 A | 7/1977 | Virag | |
| 4,066,556 A | 1/1978 | Vaillancourt | |
| 4,113,627 A * | 9/1978 | Leason | B01D 19/0031 210/446 |
| 4,121,584 A | 10/1978 | Turner et al. | |
| 4,133,627 A | 1/1979 | Kontz | |
| 4,170,056 A * | 10/1979 | Meyst | A61M 5/165 210/446 |
| 4,173,222 A | 11/1979 | Muetterties | |
| 4,198,971 A | 4/1980 | Noiles | |
| 4,200,095 A | 4/1980 | Reti | |
| 4,227,527 A | 10/1980 | De Frank et al. | |
| 4,243,032 A | 1/1981 | Howell | |
| 4,248,223 A | 2/1981 | Turner et al. | |
| 4,269,222 A | 5/1981 | Palti | |
| 4,276,170 A | 6/1981 | Vaillancourt | |
| 4,319,996 A | 3/1982 | Vincent et al. | |
| 4,372,304 A | 2/1983 | Avakian et al. | |
| 4,384,578 A | 5/1983 | Winkler | |
| 4,406,042 A | 9/1983 | McPhee | |
| 4,413,990 A | 11/1983 | Mittleman | |
| 4,428,743 A | 1/1984 | Heck | |
| 4,465,479 A | 8/1984 | Meisch | |
| 4,521,212 A * | 6/1985 | Ruschke | A61M 5/36 604/126 |
| 4,548,600 A | 10/1985 | Ruschke | |
| 4,571,244 A | 2/1986 | Knighton | |
| 4,583,979 A | 4/1986 | Palti | |
| 4,589,171 A | 5/1986 | McGill | |
| 4,601,712 A | 7/1986 | Cole et al. | |
| 4,610,781 A | 9/1986 | Bilstad et al. | |
| 4,615,694 A | 10/1986 | Raines | |
| 4,625,494 A | 12/1986 | Iwatschenko et al. | |
| 4,634,426 A | 1/1987 | Kamen | |
| 4,675,017 A | 6/1987 | Sato | |
| 4,681,563 A | 7/1987 | Deckert et al. | |
| 4,685,912 A | 8/1987 | Jones | |
| 4,795,429 A | 1/1989 | Feldstein | |
| 4,812,293 A | 3/1989 | McLaurin et al. | |
| 4,820,281 A | 4/1989 | Lawler, Jr. | |
| 4,842,588 A | 6/1989 | Jones | |
| 4,952,210 A | 8/1990 | Alchas | |
| 4,997,149 A | 3/1991 | Koch | |
| 5,102,400 A | 4/1992 | Leibinsohn | |
| 5,131,537 A | 7/1992 | Gonzales | |
| 5,188,588 A | 2/1993 | Schoendorfer et al. | |
| 5,195,987 A | 3/1993 | Karpiak | |
| 5,308,314 A | 5/1994 | Fukui et al. | |
| 5,308,333 A | 5/1994 | Skakoon | |
| 5,309,604 A | 5/1994 | Poulsen | |
| 5,389,082 A | 2/1995 | Baugues et al. | |
| 5,419,770 A | 5/1995 | Crass et al. | |
| 5,423,346 A | 6/1995 | Daoud | |
| 5,423,769 A | 6/1995 | Jonkman et al. | |
| 5,435,448 A | 7/1995 | Kempen | |
| 5,489,385 A | 2/1996 | Raabe et al. | |
| 5,542,160 A | 8/1996 | Arndt | |
| 5,681,294 A | 10/1997 | Osborne et al. | |
| 5,709,653 A | 1/1998 | Leone | |
| 5,735,826 A | 4/1998 | Richmond | |
| 5,776,109 A | 7/1998 | Urrutia | |
| 5,779,674 A | 7/1998 | Ford | |
| 5,836,923 A | 11/1998 | Mayer | |
| 5,851,202 A | 12/1998 | Carlsson | |
| 5,891,096 A | 4/1999 | Hyun et al. | |
| 5,899,665 A | 5/1999 | Makino et al. | |
| 5,902,281 A * | 5/1999 | Kraus | A61M 5/1411 604/190 |
| 5,906,598 A | 5/1999 | Giesler et al. | |
| 6,015,119 A | 1/2000 | Starchevich | |
| 6,099,512 A | 8/2000 | Urrutia | |
| 6,103,119 A | 8/2000 | Clements et al. | |
| 6,106,504 A | 8/2000 | Urrutia | |
| 6,149,631 A | 11/2000 | Haydel, Jr. | |
| 6,213,986 B1 | 4/2001 | Darling, Jr. | |
| 6,224,578 B1 | 5/2001 | Davis et al. | |
| 6,261,267 B1 | 7/2001 | Chen | |
| 6,283,945 B1 | 9/2001 | Bierman | |
| 6,336,916 B1 | 1/2002 | Bormann et al. | |
| 6,503,225 B1 | 1/2003 | Kirsch et al. | |
| RE38,145 E | 6/2003 | Lynn | |
| D479,328 S | 9/2003 | Reynolds et al. | |
| 6,685,668 B1 | 2/2004 | Cho et al. | |
| 6,833,488 B2 | 12/2004 | Bucevschi et al. | |
| 7,160,087 B2 | 1/2007 | Fathallah et al. | |

(56) References Cited

U.S. PATENT DOCUMENTS

| | | |
|---|---|---|
| 7,255,680 B1 | 8/2007 | Gharib |
| 7,722,577 B2 | 5/2010 | Miner |
| 7,892,204 B2 | 2/2011 | Kraus |
| 8,282,046 B2 | 10/2012 | Harding et al. |
| 8,523,829 B2 | 9/2013 | Miner et al. |
| 9,435,455 B2 | 9/2016 | Peret et al. |
| 9,452,255 B2 | 9/2016 | Tieck et al. |
| 2002/0156431 A1 | 10/2002 | Feith et al. |
| 2003/0048185 A1 | 3/2003 | Citrenhaum et al. |
| 2003/0220616 A1* | 11/2003 | Kraus ............ A61M 5/165 604/252 |
| 2004/0011749 A1 | 1/2004 | Hutchinson et al. |
| 2004/0254542 A1 | 12/2004 | Sacco |
| 2005/0059926 A1 | 3/2005 | Sage, Jr. et al. |
| 2005/0171491 A1 | 8/2005 | Minh Miner et al. |
| 2005/0249885 A1 | 11/2005 | Weis et al. |
| 2005/0273062 A1 | 12/2005 | Franksson et al. |
| 2006/0188407 A1 | 8/2006 | Gable et al. |
| 2006/0283544 A1 | 12/2006 | Mori et al. |
| 2007/0156118 A1 | 7/2007 | Ramsey et al. |
| 2008/0097333 A1 | 4/2008 | Henning |
| 2009/0088710 A1 | 4/2009 | Hoffman et al. |
| 2009/0093774 A1 | 4/2009 | Wang et al. |
| 2011/0276010 A1 | 11/2011 | Davis et al. |
| 2012/0171403 A1 | 7/2012 | Dodge |
| 2013/0224866 A1 | 8/2013 | Lurvey et al. |
| 2013/0338588 A1 | 12/2013 | Grimm et al. |
| 2013/0345658 A1 | 12/2013 | Browne et al. |
| 2014/0228806 A1 | 8/2014 | Alisantoso et al. |
| 2016/0339229 A1 | 11/2016 | Hung et al. |

FOREIGN PATENT DOCUMENTS

| | | |
|---|---|---|
| CN | S48-63591 | 9/1973 |
| CN | S61-206445 | 9/1986 |
| CN | 2376827 | 5/2000 |
| CN | 2453931 | 10/2001 |
| CN | 201 088 751 Y | 7/2008 |
| CN | 201342133 | 11/2009 |
| CN | 101 732 767 A | 6/2010 |
| CN | 102716533 | 10/2012 |
| CN | 102883763 | 1/2013 |
| CN | 203 107 819 U | 8/2013 |
| CN | 203 379 419 U | 1/2014 |
| CN | 104147661 | 11/2014 |
| CN | 104274487 | 1/2015 |
| DE | 41 42 625 A1 | 4/1993 |
| DE | 196 22 050 A1 | 12/1997 |
| EP | 0 001 004 A2 | 3/1979 |
| EP | 0 195 310 A1 | 9/1986 |
| EP | 0 229 354 A2 | 7/1987 |
| EP | 0 788 824 A3 | 11/1998 |
| EP | 1 181 065 B1 | 7/2003 |
| EP | 2 500 051 A1 | 9/2012 |
| FR | 2 160 821 A1 | 7/1973 |
| GB | 2 044 620 A | 10/1980 |
| JP | S50-63795 | 6/1975 |
| JP | S55-45245 | 11/1980 |
| JP | S62-170258 | 7/1987 |
| JP | H10-127778 A | 5/1998 |
| JP | H11-502771 | 3/1999 |
| JP | 2000-014745 A | 1/2000 |
| JP | 2000-229126 A | 8/2000 |
| JP | 2002522123 | 7/2002 |
| JP | 2008500879 | 1/2008 |
| JP | 2009522048 | 6/2009 |
| JP | 2009-219798 | 10/2009 |
| JP | 2013505156 | 2/2013 |
| JP | 2013525065 | 6/2013 |
| WO | 96/29104 A1 | 9/1996 |
| WO | 99/22787 A1 | 5/1999 |
| WO | 00/66200 A1 | 11/2000 |
| WO | 01/41844 A1 | 6/2001 |
| WO | 03/028525 A2 | 4/2003 |
| WO | 2005/104776 A2 | 11/2005 |
| WO | 2005/118051 A2 | 12/2005 |
| WO | 2006/083359 A2 | 8/2006 |
| WO | 2007/079049 A2 | 7/2007 |
| WO | 2008/027157 A1 | 3/2008 |
| WO | 2008/058132 | 5/2008 |
| WO | 2009/046182 A1 | 4/2009 |
| WO | 2010/030602 | 3/2010 |
| WO | 2010/030602 A1 | 3/2010 |
| WO | 2011/139517 | 11/2011 |
| WO | 2011/139517 A1 | 11/2011 |
| WO | 2013/070337 A1 | 5/2013 |
| WO | 2013/188103 A1 | 12/2013 |

OTHER PUBLICATIONS

Shift Labs, DripAssist Infusion Rate Monitor, http://www.shiftlabs.com/dripassist-human-health, pp. 1-5, Apr. 3, 2017.

Brown, et al.: "Non-contact laser sealing of thin polyester food packaing films", Optics and Lasers Engineering, Elsevier, Amsterdam, NL, vol. 50, No. 10, Apr. 2, 2012, pp. 1466-1473, XP028500061.

* cited by examiner

IV MEMBRANE ATTACHMENT SYSTEMS AND METHODS

RELATED APPLICATIONS

This application is a divisional of U.S. patent application Ser. No. 15/078,722, filed Mar. 23, 2016, and entitled IV MEMBRANE ATTACHMENT SYSTEMS AND METHODS, which claims priority to U.S. Provisional Patent Application Ser. No. 62/138,718, filed Mar. 26, 2015, and entitled IV MEMBRANE ATTACHMENT SYSTEMS AND METHODS, which are incorporated herein in their entirety.

BACKGROUND

The present invention is generally directed to systems and methods for intravenous ("IV") delivery, by which fluids can be administered directly to a patient. More particularly, the present invention is directed systems and methods for manufacturing components of an intravenous delivery system. An intravenous delivery system according to the invention is used broadly herein to describe components used to deliver the fluid to the patient, for use in arterial, intravenous, intravascular, peritoneal, and/or non-vascular administration of fluid. Of course, one of skill in the art may use an intravenous delivery system to administer fluids to other locations within a patient's body.

One common method of administering fluids into a patient's blood flow is through an intravenous delivery system. In many common implementations, an intravenous delivery system may include a liquid source such as a liquid bag, a drip chamber used to determine the flow rate of fluid from the liquid bag, tubing for providing a connection between the liquid bag and the patient, and an intravenous access unit, such as a catheter that may be positioned intravenously in a patient. An intravenous delivery system may also include a Y-connector that allows for the piggybacking of intravenous delivery systems and for the administration of medicine from a syringe into the tubing of the intravenous delivery system.

It is a generally good practice to remove air from intravenous delivery systems that access a patient's blood flow. While this concern is critical when accessing arterial blood, it is also a concern when accessing the venous side. Specifically, if air bubbles are allowed to enter a patient's blood stream while receiving the intravenous administration of fluids, the air bubbles can form an air embolism and cause serious injury to a patient.

Normally, in a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an intravenous delivery system for use in the intravenous administration of fluids, the complete removal of air bubbles can be a time consuming process. The process may also lead to contamination of the intravenous delivery system by inadvertently touching a sterile end of the intravenous delivery system. Typically, when an intravenous delivery system is primed, a clamp is closed to prevent fluid from moving from a drip chamber through the tubing. The intravenous delivery system may then be attached to an IV bag or bottle. Once attached, the drip chamber, which is typically made of a clear flexible plastic, may be squeezed to draw the fluid out of the IV bag or bottle and into the drip chamber. The drip chamber may be allowed to fill about ¼ to ½ full when the clamp is opened to allow fluid to flow through the tube to an end of the intravenous delivery system.

This initial process, however, typically traps air in tubing which must be removed. For example, the flow of the fluid through the tubing of the intravenous delivery system may be turbulent and can entrap air within the tube as the boundary layer between the fluid and the tubing is sheared. The flow rate out of the drip chamber may be higher than the flow rate of fluid entering the drip chamber. This can cause a bubble ladder to form as air is sucked from the drip chamber into the tubing.

Additionally, air bubbles may be generated as drops of fluid strike the surface of the pool of fluid within the drip chamber. These air bubbles can be pulled into the tubing of the IV set from the drip chamber. This problem may be aggravated in pediatric applications where the drip orifice may be smaller, which may result in increased turbulence.

To remove air bubbles from the intravenous delivery system, fluid from the IV bag or bottle may be allowed to flow through the tubing while an attendant taps the tubing to encourage the air bubbles out the end of the intravenous delivery system. As the fluid is allowed to flow out of the intravenous delivery system to clear air bubbles from the tubing, the fluid may be allowed to flow into a waste basket or other receptacle. During this procedure, the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the intravenous delivery system. More specifically, if the intravenous delivery system includes a Y-connector, air bubbles may be removed at the Y-connector by a syringe. This method still requires additional time and attention, and may also carry risk of contamination of the liquid to be delivered.

To address the difficulties of removing bubbles from an intravenous delivery system, various prior art intravenous delivery systems have employed a membrane for filtering air from the fluid as it flows through the intravenous delivery system. For example, oftentimes a membrane may be placed in the bottom of the drip chamber so that fluid flowing out of the drip chamber must pass through the membrane. The membrane can be configured to allow the passage of fluid while blocking the passage of air. In this way, bubbles are prevented from passing into the tubing leading to the patient. Similarly, a membrane can be included in the connector that couples the tubing to a catheter to block any air present in the tubing from passing into the patient's vasculature.

The use of air filtering membranes in these prior art intravenous delivery system designs have been beneficial. However, such membranes introduce new manufacturing challenges. Ordinary welding processes are typically used to attach materials with similar melting points together. The materials at the weld interface can be melted and thereby mixed together. However, membranes may be composed of materials with specific hydrodynamic properties, which may have melting points significantly different from those of the materials used in adjacent components of the intravenous delivery system. Thus, traditional welding techniques may not be effective for attaching the membrane in place.

Further, in order to extend the benefits of health care to lower income areas and individuals, it would be beneficial to reduce the manufacturing cost and complexity of processes used to make existing intravenous delivery systems. Yet further, increasing the reliability of such processes may reduce the risk that the intravenous delivery system will fail to operate properly due to a manufacturing defect.

BRIEF SUMMARY OF THE INVENTION

Embodiments of the present invention are generally directed to an intravenous delivery system with an anti-run-dry membrane. The intravenous delivery system may have a liquid source containing a liquid to be delivered to a patient, a drip unit containing the anti-run-dry membrane, and tubing. The tubing may have a first end connectable to the liquid source, and a second end connectable to a vent cap and/or an intravenous delivery unit.

The anti-run-dry membrane may be formed of a hydrophilic material, and may have a plurality of pores that permit the liquid to flow through the anti-run-dry membrane, while resisting passage of air through the anti-run-dry membrane. The anti-run-dry membrane may be secured to a seat formed on an exterior wall of the drip unit to prevent air from flowing from the top part of the drip unit to the bottom part of the drip unit, through the anti-run-dry membrane. The anti-run-dry membrane may be secured to the seat through the use of an attachment component.

In some embodiments, the drip unit may have a secondary exterior wall that cooperates with the exterior wall to define the drip chamber, and also acts as the attachment component. The anti-run-dry membrane may be captured between the exterior wall and the secondary exterior wall. The exterior wall and the second exterior wall may both be fully formed, and then assembled with the anti-run-dry membrane in its proper place relative to them. In such an embodiment, the secondary exterior wall may have an attachment feature that mates with the exterior wall. Alternatively, the exterior wall or the secondary exterior wall may be formed, and the anti-run-dry membrane may be placed in the desired position relative to it. Then, the other of the two (the exterior wall or the secondary exterior wall) may be molded at its final position relative to the anti-run-dry membrane, thereby capturing the anti-run-dry membrane via insert molding.

In alternative embodiments, the attachment component may be a washer with a membrane facing surface that is placed in contact with the anti-run-dry membrane to keep the anti-run-dry membrane in place. The washer may be secured to the exterior wall via ultrasonic welding, solvent bonding, laser welding, or the like. The membrane facing surface may have a plurality of engagement elements that protrude through the anti-run-dry membrane. Each of the engagement elements may have a distal end that can be butt welded or otherwise attached to the seat to keep the anti-run-dry membrane in place. In the alternative, the rim of the washer may be secured to the interior surface of the exterior wall via shear welding or the like.

In other alternative embodiments, the attachment component may be an adhesive ring that is applied to the anti-run-dry membrane and positioned on the seat when the anti-run-dry membrane is in place. The adhesive ring may be formed of a pressure-sensitive adhesive. Thus, in response to compression of the adhesive ring, the adhesive ring may adhere to the seat and to the attachment surface of the anti-run-dry membrane.

If desired, interference features may be used to create an interference fit between the anti-run-dry membrane and the interior of the exterior wall. Such interference features may on the anti-run-dry membrane, and may protrude radially outward to engage the interior of the exterior wall. Alternatively, such interference features may be on the interior of the exterior wall, and may protrude radially inward to engage the periphery of the anti-run-dry membrane. In either case, the resulting interference fit may help to keep the anti-run-dry membrane in place as other manufacturing steps are performed, without causing excessive wrinkling or other deformation of the anti-run-dry membrane.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation.

Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
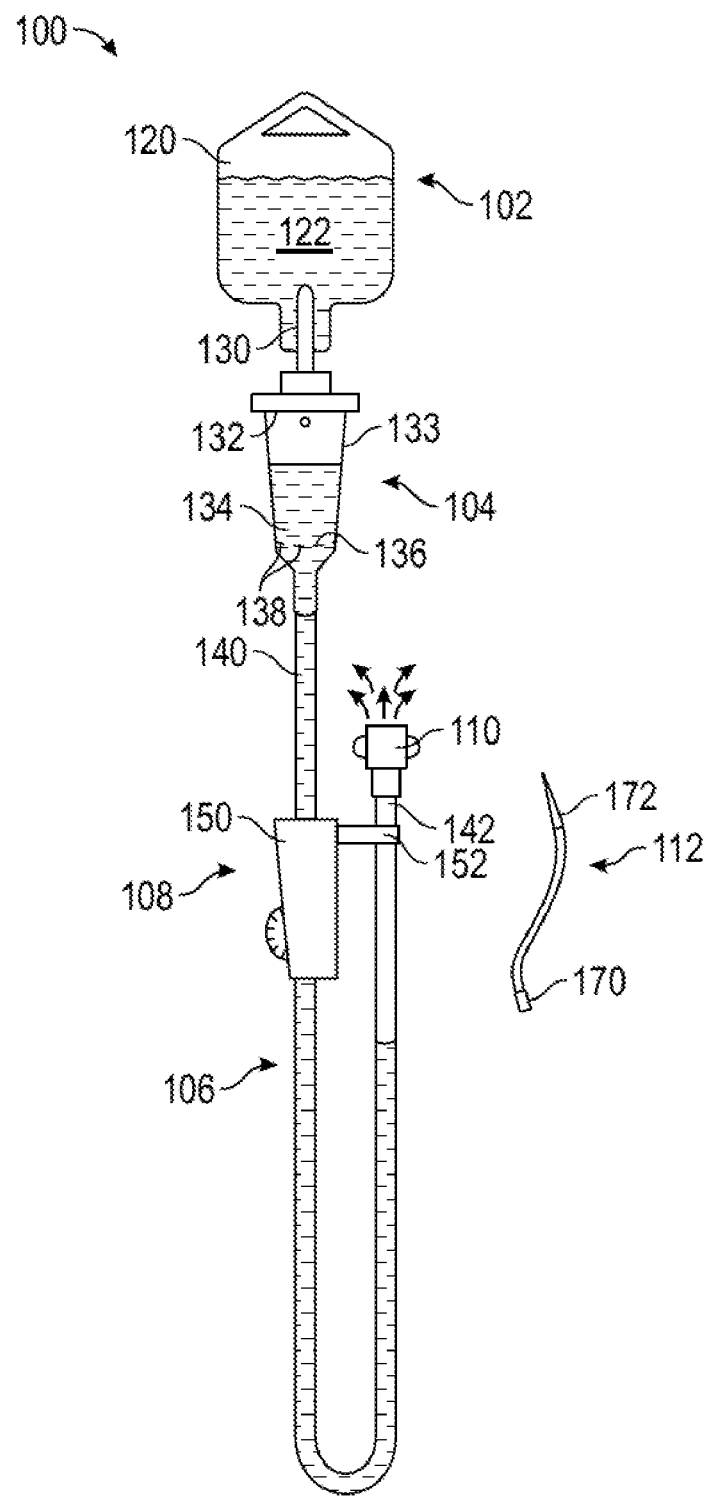
FIG. 1 is a front elevation view of an intravenous delivery system according to one embodiment.

Referring to FIG. 1, a front elevation view illustrates an intravenous delivery system 100 according to one embodiment. As shown, the intravenous delivery system 100 may have a number of components, which may include a liquid source 102, a drip unit 104, tubing 106 a retention unit 108, a vent cap 110, and an intravenous access unit 112. The manner in which these components are illustrated in FIG. 1 is merely exemplary; those of skill in the art will recognize that a wide variety of intravenous delivery systems exist. Thus, the various components the intravenous delivery system 100 may be omitted, replaced, and/or supplemented with components different from those illustrated.

The liquid source 102 may have a container containing a liquid 122 to be delivered intravenously to a patient. The liquid source 102 may, for example, have a membrane 120, which may be formed of a translucent, flexible polymer or the like. The membrane 120 may thus have a baglike configuration. The membrane 120 may be shaped to contain the liquid 122.

The drip unit 104 may be designed to receive the liquid 122 from the membrane 120 in a measured rate, for example, as a series of drips occurring at a predictable, consistent rate. The drip unit 104 may be positioned below the membrane 120 so as to receive the liquid 122 via gravity feed. The drip unit 104 may have a receiving device 130 that receives the liquid 122 from the liquid source 102, a drip feature 132 that determines the rate at which the liquid 122 is received by the drip unit 104, and an exterior wall 133 that defines a drip chamber 134 in which the liquid 122 is collected. An anti-run-dry membrane 136 may be positioned within the drip chamber 134 to enable a fluid column of significant length to be maintained within the tubing 106 after cessation of flow of the liquid 122 into the tubing 106, without permitting significant air to flow into the tubing 106 through the anti-run-dry membrane 136.

The tubing 106 may be standard medical grade tubing. The tubing 106 may be formed of a flexible, translucent material such as a silicone rubber. The tubing 106 may have a first end 140 and a second end 142. The first end 140 may be coupled to the drip unit 104, and the second end 142 may be coupled to the vent cap 110, such that the liquid 122 flows from the drip unit 104 to the vent cap 110, through the tubing 106.

The retention unit 108 may be used to retain various other components of the intravenous delivery system 100. As shown, the retention unit 108 may have a main body 150 and an extension 152. Generally, the tubing 106 may be connected to the main body 150 proximate the first end 140, and to the extension 152 proximate the second end 142. Various racks, brackets, and/or other features may be used in addition to or in place of the retention unit 108.

The vent cap 110 may be coupled to the second end 142 of the tubing 106. The vent cap 110 may have a vent, such as a hydrophobic membrane that is substantially permeable to air, but not to the liquid 122. Thus, air from within the vent cap 110 can be vented from the intravenous delivery system 100, with limited leakage of the liquid 122 from the intravenous delivery system 100.

The intravenous access unit 112 may be used to supply the liquid 122 to the vascular system of the patient. The intravenous access unit 112 may have a first end 170 and an access end 172. The first end 170 may be connectable to the second end 142 of the tubing 106 in place of the vent cap 110. Thus, when the intravenous delivery system 100 is fully primed, the intravenous access unit 112 may be coupled to the second end 142 of the tubing 106 in place of the vent cap 110. In alternative embodiments (not shown), various connectors such as Y-adapters may be used to connect the first end 170 of the intravenous access unit 112 to the tubing 106 without detaching the vent cap 110 from the second end 142 of the tubing 106.

The intravenous delivery system 100 may be primed by connecting the components (except for the intravenous access unit 112) together as illustrated in FIG. 1, and then allowing the liquid 122 to gravity feed through the drip unit 104 and the tubing 106 into the vent cap 110. If desired, the drip unit 104 may be squeezed or otherwise pressurized to expedite flow of the liquid 122 through the tubing 106.

As the liquid 122 flows through the tubing 106, air may become entrained in the liquid 122. This air may move from the first end 140 of the tubing 106, toward the second end 142 of the tubing 106, along with the column of liquid 122. This entrained air may gather into bubbles proximate the second end 142 of the tubing 106. The vent cap 110 may be designed to receive the liquid 122 to permit such air bubbles to be vented from the intravenous delivery system 100 through the vent cap 110.

Once the liquid 122 stops flowing into the liquid 122, for example, due to depletion of the liquid 122 in the liquid source 102, the anti-run-dry membrane 136 may act to restrict motion of air into the tubing 106. The anti-run-dry membrane 136 may have a plurality of pores 138, each of which has a size that causes the formation of a meniscus of the liquid 122 underneath the anti-run-dry membrane 136. Each meniscus may, via capillary action, contribute to the support of a column of the liquid 122 in the tubing 106. The anti-run-dry membrane 136 may be designed to facilitate support of a column of the liquid 122 of significant length before permitting air to enter the column. The longer the column that can be supported, the more robust the intravenous delivery system 100 will be to different operational conditions.

The anti-run-dry membrane 136 may be secured to the exterior wall 133 of the drip unit 104 through the use of various manufacturing methods. Although various welding techniques are known to be effective for securing plastic components together, such welding techniques often rely on the components having similar melting points so that they can melt together and intermix at the weld interface. Attachment of the anti-run-dry membrane 136 to the exterior wall 133 of the drip unit 104 may present a unique challenge due to the likely disparity in melting points between these two components.

More specifically, the exterior wall 133 of the drip unit 104 may be formed of any of a variety of materials such as PVC, SBC, and TPO. Such materials often have a melting point within the range of about 190° C. to about 210° C. By contrast, the anti-run-dry membrane 136 may be formed of a material such as Polyethersulfone (PES). In many formulations, PES may have a melting point within the range of about 250° C. to about 350° C. Accordingly, traditional fabrication techniques may not provide secure attachment of the anti-run-dry membrane 136 to the exterior wall 133. The exterior wall 133 may begin melting long before the anti-run-dry membrane 136 has reached its melting point; thus, the portion of the exterior wall 133 to which the anti-run-dry membrane 136 is to be attached may lose too much of its shape and rigidity before the anti-run-dry membrane 136 begins to melt.

In some embodiments, an attachment component (not shown in FIG. 1) may be used to mechanically attach the anti-run-dry membrane 136 to the exterior wall 133. A generalized method for attaching an anti-run-dry membrane to an exterior wall will be set forth in connection with FIG. 2, as follows.

Figure 2:
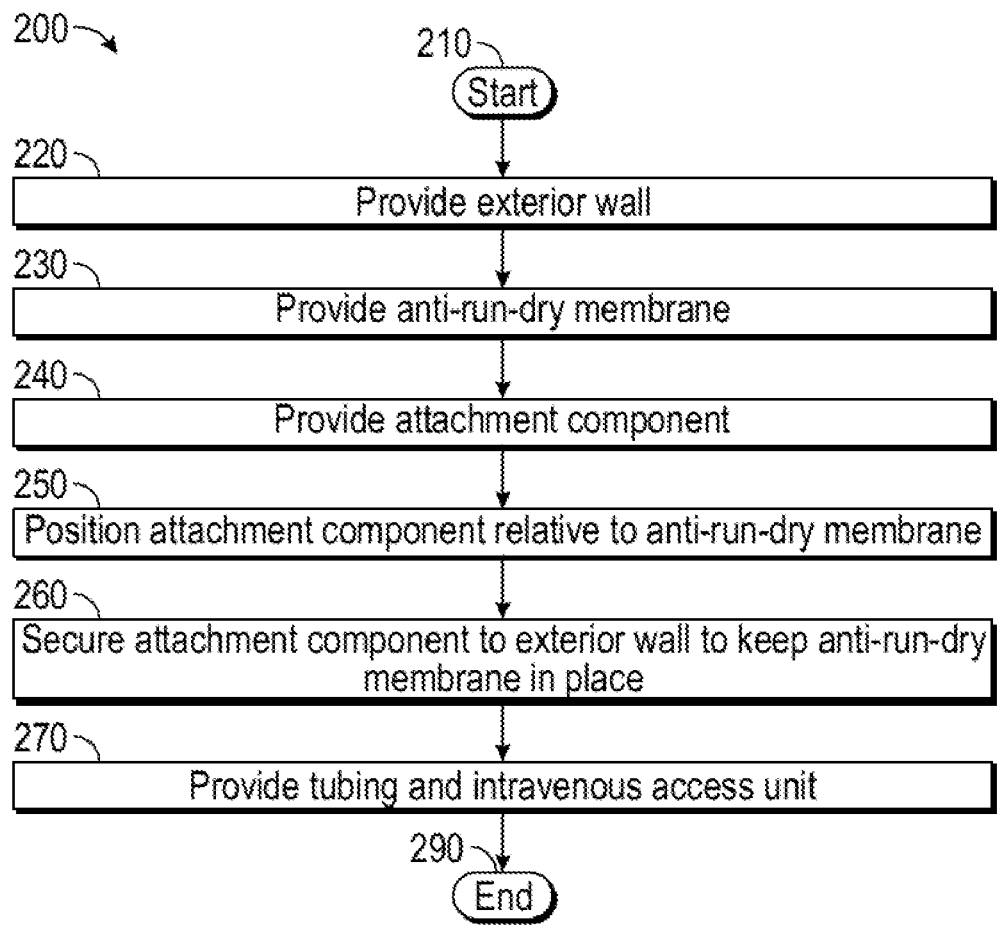
FIG. 2 is a flowchart diagram illustrating a method of manufacturing a drip chamber for an intravenous delivery system, according to one embodiment.

Referring to FIG. 2, a flowchart diagram illustrates a method 200 of manufacturing a drip chamber for an intravenous delivery system, according to one embodiment. The method 200 will be described with reference to the intravenous delivery system 100 of FIG. 1. However, those of skill in the art will recognize that the method 200 may be carried out with different intravenous delivery systems. Similarly, the intravenous delivery system 100 may be manufactured through the use of methods other than that of FIG. 2.

The method 200 may start 210 with a step 220 in which the exterior wall 133 of the drip unit 104 is provided. The exterior wall 133 may be made of a polymer such as PVC, SBC, and TPO, and may be manufactured through the use of various processes, including but not limited to injection molding, blow molding, casting, and/or the like. The drip chamber 134 may be at least partially defined by the exterior wall 133. Other components such as the drip feature 132 may cooperate with the exterior wall 133 to fully define the drip chamber 134. Notably, in some embodiments, the exterior wall 133 may not be provided until after the anti-run-dry membrane 136 has already been positioned; the exterior wall 133 may then be formed with the anti-run-dry membrane 136 in place, as will be described in connection with FIG. 5.

In a step 230, the anti-run-dry membrane 136 may be provided. The anti-run-dry membrane 136 may be made of a polymer such as Polyethersulfone (PES), and may be manufactured through the use of the processes listed above, by way of example. The processes used to form the anti-run-dry membrane 136 may be tuned to provide the pores 138 of the anti-run-dry membrane 136 with the desired size, which may be optimized to permit passage of the liquid 122 through the anti-run-dry membrane 136, while limiting passage of air through the anti-run-dry membrane 136.

In a step 240, the attachment component may be provided. The attachment component may be made of various materials and/or formed through the use of various methods known in the art, depending on the configuration of the attachment component. In some embodiments, the attachment component may be made of a plastic material similar to that of the exterior wall 133 to facilitate attachment of the attachment component to the exterior wall 133. For attachment methods such as welding, it may be advantageous for the attachment component to have a melting point similar to that of the exterior wall 133. For solvent attachment, adhesive bonding, and/or other methods, there may desirably be a high degree of similarity in chemical compositions between the attachment component and the exterior wall 133.

In a step 250, the attachment component may be positioned relative to the anti-run-dry membrane 136. In a step 260, the attachment component may be secured to the exterior wall 133 to keep the anti-run-dry membrane 136 in place. Any of a variety of attachment methods may be used to accomplish this; some examples will be shown and described subsequently.

In a step 270, other parts of the intravenous delivery system 100 may be provided. These parts may include the tubing 106 and the intravenous access unit 112 and/or other components that are to be packaged and/or provided by the manufacturer along with the drip unit 104. The method 200 may then end 290.

As indicated previously, various different attachment components may be used to secure the anti-run-dry membrane 136 to the exterior wall 133. Various attachment methods may be used, depending on the type of attachment component to be used. Exemplary attachment components and methods will be shown and described in connection with FIGS. 3 through 9, as follows.

Figure 3:
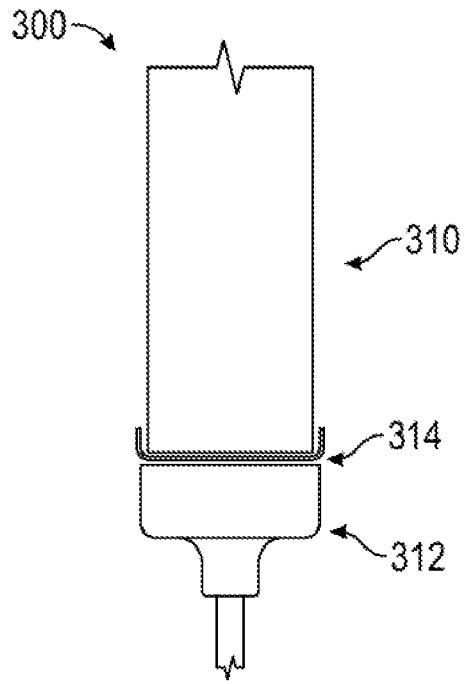
FIG. 3 is a front elevation, exploded view of a portion of a drip unit according to one embodiment, illustrating the use of an attachment component in the form of a secondary exterior wall attachable to the exterior wall to capture the anti-run-dry membrane.

Referring to FIG. 3, a front elevation, exploded view illustrates a portion of a drip unit 300 according to one embodiment. As shown, the drip unit 300 may have an exterior wall 310, an attachment component in the form of a secondary exterior wall 312, and an anti-run-dry membrane 314. The exterior wall 310 and the secondary exterior wall 312 may be secured together such that the anti-run-dry membrane 314 is sandwiched between them; thus, the anti-run-dry membrane 314 may be securely mechanically retained. The drip unit 300 may have a drip feature 132 like that of FIG. 1; this has been omitted from FIG. 3 and from other embodiments for clarity.

The drip unit 300 may advantageously allow the anti-run-dry membrane 314 to be secured in place within the drip unit 300 synchronously with assembly of the drip unit 300 via attachment of the exterior wall 310 to the secondary exterior wall 312. The configuration and operation of the drip unit 300 will be shown and described in greater detail in connection with FIG. 4.

Figure 4:
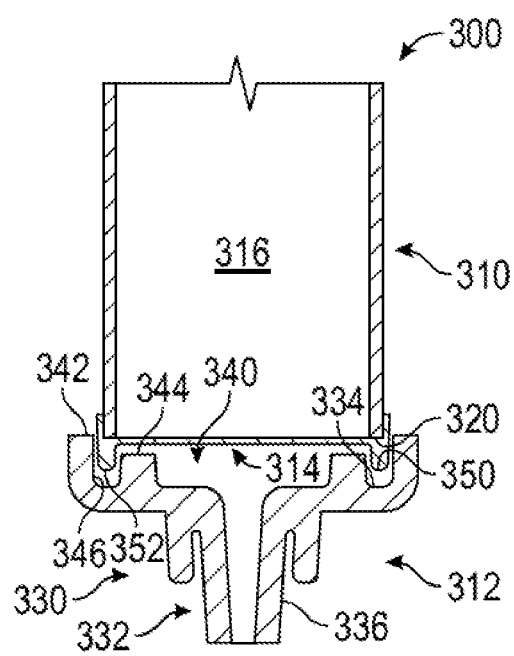
FIG. 4 is a front elevation, section view of a portion of the drip unit of FIG. 3, illustrating how the anti-run-dry membrane is captured between the exterior wall and the secondary exterior wall.

Referring to FIG. 4, a front elevation, section view illustrates a portion of the drip unit 300 of FIG. 3, in greater detail. As shown, the exterior wall 310 and the secondary exterior wall 312 may cooperate to define a drip chamber 316 that receives the liquid 122 from a liquid source such as the liquid source 102 of FIG. 1. The exterior wall 310 may have a generally tubular and/or frustoconical shape, with a seat 320 in the form of an annular surface defined by the end of the tubular and/or frustoconical shape. The secondary exterior wall 312 may have a generally discoid shape with an attachment portion 330 and an outlet portion 332 protruding from the attachment portion 330.

The attachment portion 330 may be secured to the exterior wall 310 and the anti-run-dry membrane 314, and the outlet portion 332 may be coupled to the first end 140 of the tubing 106 to deliver the liquid 122 to the first end 140. Thus, the attachment portion 330 may have an attachment surface 334 designed to contact the anti-run-dry membrane 314, and the outlet portion 332 may have tubing interface 336 configured to be connectable to the first end 140 of the tubing 106.

The attachment portion 330 may also have an attachment feature 340 that facilitates mating of the secondary exterior wall 312 with the exterior wall 310. In the embodiment of FIG. 4, the attachment feature 340 may include an outer ring 342 and an inner ring 344, which may be generally concentric with each other, and may protrude toward the exterior wall 310. The outer ring 342 and the inner ring 344 may be spaced apart to define a recess 346 between the outer ring 342 and the inner ring 344. The outer ring 342 and the inner ring 344 may be spaced apart in such a manner that the end of the generally tubular and/or frustoconical shape of the exterior wall 310 may be captured between the outer ring 342 and the inner ring 344.

The attachment surface 334 may be a generally annular surface positioned in a recess defined between the outer ring 342 and the inner ring 344. The anti-run-dry membrane 314 may have a first attachment surface 350 proximate its periphery, facing the exterior wall 310, and a second attachment surface 352 proximate its periphery, facing the secondary exterior wall 312. When the exterior wall 310 and the secondary exterior wall 312 are assembled, the anti-run-dry membrane 314 may be sandwiched between the exterior wall 310 and the secondary exterior wall 312 as shown, such that the first attachment surface 350 abuts the seat 320 of the exterior wall 310 and the second attachment surface 352 abuts the attachment surface 334 of the secondary exterior wall 312.

If desired, the anti-run-dry membrane 314, the outer ring 342, and the inner ring 344 may be dimensioned and positioned such that the end of the exterior wall 310 has an interference fit with either or both of the outer ring 342 and the inner ring 344 when the anti-run-dry membrane 314 is captured between the attachment feature 340 and the end of the exterior wall 310, as shown. More particularly, the interior diameter at the end of the exterior wall 310 may be slightly smaller than the exterior diameter of the inner ring 344 with added thickness of the anti-run-dry membrane 314. Additionally or alternatively, the exterior diameter at the end of the exterior wall 310, with the added thickness of the anti-run-dry membrane 314, may be slightly larger than the interior diameter of the outer ring 342. Additionally or alternatively, the wall thickness of the end of the exterior wall 310, with the added thickness of the portions of the anti-run-dry membrane 314 that will be positioned interior to and exterior to it, may be slightly smaller than the width of the recess 346, so as to provide an interference fit between the recess 346 and the end of the exterior wall 310 and the anti-run-dry membrane 314.

If desired, one or more of the outer ring 342, the inner ring 344, and/or the end of the exterior wall 310 may have a tapered shape that facilitates initial assembly of the exterior wall 310 and the secondary exterior wall 312. The presence of such a tapered shape may require some compressive force applied to urge the exterior wall 310 toward the secondary exterior wall 312, thereby urging the end of the exterior wall 310 to seat fully within the recess 346. Such tapered shapes may facilitate assembly of the exterior wall 310 and the secondary exterior wall 312 with any of the interference fits described above.

If desired, such interference fits may, alone, define a seal between the anti-run-dry membrane 314 and the periphery of the exterior wall 310, and/or provide a pullout force sufficient that no other attachment method need be used to attach the exterior wall 310 to the secondary exterior wall 312. Alternatively, any of a wide variety of attachment methods may be used to secure the secondary exterior wall 312 to the exterior wall 310. Such attachment methods may include, but need not be limited to, solvent-based chemical bonding, ultrasonic welding, laser welding, thermal welding, adhesive bonding, mechanical fastening such as snap fitting via one or more snap features (not shown), or the like.

In alternative embodiments, the components of a drip unit need not all be formed prior to assembly. Insert molding and other techniques may be used to form one or more components of a drip unit with remaining components already in place. One such embodiment will be shown and described in connection with FIG. 5.

Figure 5:
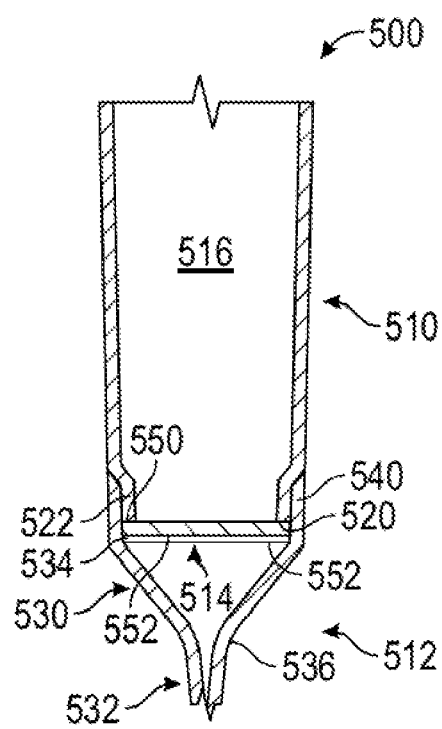
FIG. 5 is a front elevation, section view of a portion of a drip unit according to another embodiment, illustrating insert molding of the exterior wall with the anti-run-dry membrane in place.

Referring to FIG. 5, a front elevation, section view illustrates a portion of a drip unit 500 according to another embodiment. As shown, the drip unit 500 may have an exterior wall 510, an attachment component in the form of a secondary exterior wall 512, and an anti-run-dry membrane 514. The exterior wall 510 and the secondary exterior wall 512 may be secured together such that the anti-run-dry membrane 514 is sandwiched between them; thus, the anti-run-dry membrane 514 may be securely mechanically retained. However, rather than forming the exterior wall 510 prior to positioning of the anti-run-dry membrane 514, the exterior wall 510 may be insert molded in position relative to the secondary exterior wall 512 and the anti-run-dry membrane 514 so that no separate assembly step need be carried out.

As shown, the exterior wall 510 and the secondary exterior wall 512 may cooperate to define a drip chamber

516 that receives the liquid 122 from a liquid source such as the liquid source 102 of FIG. 1. The exterior wall 510 may have a generally tubular and/or frustoconical shape, with a seat 520 in the form of an annular surface defined by the end of the tubular and/or frustoconical shape, and reduced diameter portion 522 adjacent to the seat 520. The secondary exterior wall 512 may have a generally conical shape with an attachment portion 530 and an outlet portion 532 protruding from the attachment portion 530.

The attachment portion 530 may be secured to the exterior wall 510 and the anti-run-dry membrane 314, and the outlet portion 532 may be coupled to the first end 140 of the tubing 106 to deliver the liquid 122 to the first end 140. Thus, the attachment portion 530 may have an attachment surface 534 designed to contact the anti-run-dry membrane 514, and the outlet portion 532 may have tubing interface 536 configured to be connectable to the first end 140 of the tubing 106. The attachment surface 534 may simply be part of a recess, groove, or step formed in the interior surface of the secondary exterior wall 512, adjacent to the anti-run-dry membrane 514. The membrane 514 may be sized to fit in the recess, groove, or step.

The attachment portion 530 may also have an annular wall 540 that facilitates engagement of the exterior wall 510 with the secondary exterior wall 512. More specifically, the annular wall 540 may be sized to receive the reduced diameter portion 522 of the exterior wall 510. The membrane 514 may have a first attachment surface 550 that abuts the attachment portion 530, and a second attachment surface 552 that abuts the attachment surface 534 when the drip unit 500 is fully assembled.

The exterior wall 510 may be manufactured via injection molding. More specifically, the secondary exterior wall 512 and the anti-run-dry membrane 514 may first be formed. Then, the anti-run-dry membrane 514 may be positioned relative to the secondary exterior wall 512, such that the second attachment surface 552 is in contact with the attachment surface 534 of the secondary exterior wall 512, as shown in FIG. 5. Then, the secondary exterior wall 512 and the anti-run-dry membrane 514 may be positioned in a mold for a molding process such as injection molding.

The exterior wall 510 may then be molded in place through the use of the mold. The mold may be opened to release the drip unit 500, which may be in a fully assembled state, as shown in FIG. 5. The diameter portion 522 of the exterior wall 510 may engage the annular wall 540 of the secondary exterior wall 512 such that the exterior wall 510 and the secondary exterior wall 512 remain assembled, and the anti-run-dry membrane 514 remains trapped between the seat 520 of the exterior wall 510 and the attachment surface 534 of the secondary exterior wall 512.

Advantageously, no additional assembly and/or attachment processes need be used to secure the exterior wall 510 and the secondary exterior wall 512 together. The insert molding process may form a secure, sealed attachment between the exterior wall 510 and the secondary exterior wall 512. However, if desired, one or more additional attachment processes, such as solvent-based chemical bonding, ultrasonic welding, laser welding, thermal welding, adhesive bonding, and mechanical fastening may be used to further secure the exterior wall 510 and the secondary exterior wall 512 together. The membrane may also be placed in the mold and over-molded as exterior wall 510 is formed. The exterior wall and membrane could then be attached to secondary exterior wall 512 through various attachment techniques as mentioned above.

In alternative embodiments, insert molding may be used in various different ways to secure an anti-run-dry membrane to an exterior wall. For example, in some embodiments (not shown), the anti-run-dry membrane may be insert molded into a module such as a disk. The module may then be secured to the exterior wall through the use of any known attachment method, including but not limited to those listed above.

In other alternative embodiments, a drip unit may have an attachment component that does not define a boundary of the drip chamber. Such an attachment component may reside within the drip chamber to secure an anti-run-dry membrane to an interior wall. One example of such an embodiment will be shown and described in connection with FIGS. 6A through 7.

Figure 6A:
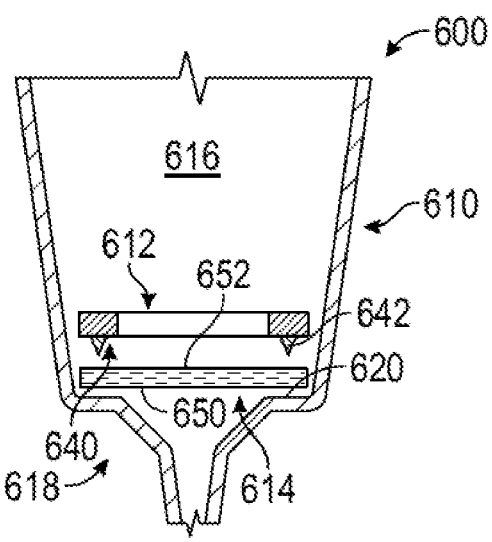
FIGS. 6A and 6B are a side elevation, exploded section view of a portion of a drip unit according to another embodiment, with an attachment component in the form of a washer that keeps the anti-run-dry membrane in place, and a perspective view of the washer, respectively.

Referring to FIG. 6A, a side elevation, exploded section view illustrates a portion of a drip unit 600 according to another embodiment. As shown, the drip unit 600 may have an exterior wall 610, an attachment component in the form of a washer 612, and an anti-run-dry membrane 614. The exterior wall 610 and the washer 612 may be secured together such that the anti-run-dry membrane 614 is sandwiched between them; thus, the anti-run-dry membrane 614 may be securely mechanically retained within a drip chamber 616 defined by the exterior wall 610. Since the washer 612 does not form a boundary of the drip chamber 616, a hermetic seal need not necessarily be formed between the washer 612 and the exterior wall 610.

As shown, the exterior wall 610 may have a generally tubular and/or frustoconical shape, with a shelf 618 with a generally annular shape. A seat 620 in the form of an annular surface may exist on the interior of the shelf 618. The membrane 614 may have a first attachment surface 650 facing toward the seat 620, and a second attachment surface 652 facing toward the washer 612. The washer 612 may have a generally annular shape, with an attachment surface in the form of a membrane-facing surface 640 having a plurality of anchoring elements 642 extending therefrom. Each of the anchoring elements 642 may have a distal end with a sharpened tip capable of piercing the anti-run-dry membrane 614.

When the anti-run-dry membrane 614 is to be secured to the exterior wall 610, the anti-run-dry membrane 614 may first be positioned with the first attachment surface 650 resting on the seat 620 of the exterior wall 610. Then, the washer 612 may be positioned on the anti-run-dry membrane 614, with the distal ends of the anchoring elements 642 resting on the second attachment surface 652 of the anti-run-dry membrane 614. The washer 612 may be driven toward the seat 620 so that the anchoring elements 642 penetrate the anti-run-dry membrane 614. The anchoring elements 642 may be driven through the anti-run-dry membrane 614 until they emerge from the first attachment surface 650 and make contact with the seat 620.

With the distal ends of the anchoring elements 642 in contact with the seat 620, the distal ends of the anchoring elements 642 may be secured to the seat 620. This may be done via any of the attachment procedures mentioned previously. In some embodiments, ultrasonic welding, solvent bonding, and/or laser welding may be used. The distal ends of the anchoring elements 642 may naturally serve as energy directors for ultrasonic vibrations, focal points for heat flow, and/or the like, and may thus preferentially melt into engagement with the seat 620. Thus, the distal ends of the anchoring elements 642 may be readily butt welded to the seat 620. As with other types of attachment components, the washer 612 may advantageously be made of a material similar to that of the exterior wall 610, so as to provide compatibility for the selected method of attaching the washer 612 to the exterior wall 610.

Figure 6B:
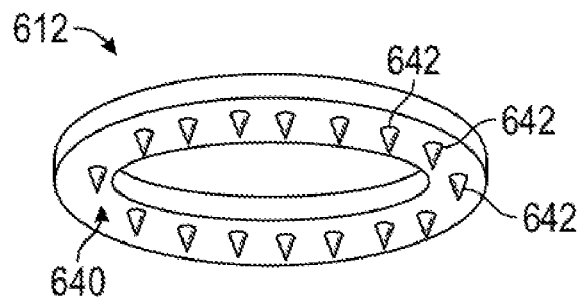

Referring to FIG. 6B, a perspective view illustrates the washer 612 of the drip unit 600 of FIG. 6A in greater detail. The number, shape, and arrangement of the anchoring elements 642 are merely exemplary; many different anchoring element configurations may be used within the scope of the present disclosure. The drip unit 600 with the washer 612 attached to the exterior wall 610 will be shown and described in greater detail in connection with FIG. 7.

Figure 7:
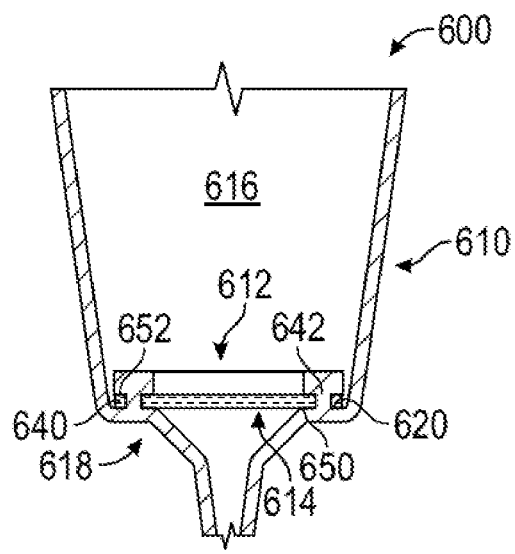
FIG. 7 is a front elevation, section view of a portion of the drip unit of FIGS. 6A and 6B, in a fully assembled state.

Referring to FIG. 7, a front elevation, section view illustrates a portion of the drip unit 600 of FIGS. 6A and 6B, in a fully assembled state. As shown, the anchoring elements 642 of the washer 612 may melt at their distal ends, and fuse with the seat 620 of the exterior wall 610. Thus, the washer 612 may securely trap the anti-run-dry membrane 614 in place against the seat 620. Fluid, such as the liquid 122, flowing from the upper portion of the drip chamber 616 to the lower portion of the drip chamber 616 may have to move through the interior of the washer 612, and through the anti-run-dry membrane 614, in order to reach the bottom portion of the drip chamber 616.

If desired, the anchoring elements 642 may be designed in such a manner that they form a hermetic seal around the periphery of the anti-run-dry membrane 614. This may help to ensure that air is not able to move around the edges of the anti-run-dry membrane 614 and into the bottom portion of the drip chamber 616. Alternatively or additionally, a separate procedure may be used to provide a seal around the exterior of the washer 612. Alternatively or additionally, the anti-run-dry membrane 614 may be sized such that its outer edge is sized to contact the interior surface of the exterior wall 310, proximate the seat 620. This may help ensure that fluids must pass through the anti-run-dry membrane 614 to reach the bottom portion of the drip chamber 616. If desired, an interference fit between the anti-run-dry membrane 614 and the interior surface of the exterior wall 610 may be used to further restrict fluid flow around the edges of the anti-run-dry membrane 614.

As yet another alternative embodiment, the washer 612 may be secured, at its outer edges, to the interior surface of the exterior wall 610. For example, in addition to or in the alternative to the use of a butt weld or other attachment procedure that attaches the anchoring elements 642 directly to the seat 620, a shear weld or other attachment may be used to attach the rim of the washer 612 to the interior surface of the exterior wall 610.

As mentioned previously, many different engagement element configurations may be used within the scope of the present disclosure. One additional exemplary configuration will be shown and described in connection with FIG. 8.

Figure 8:
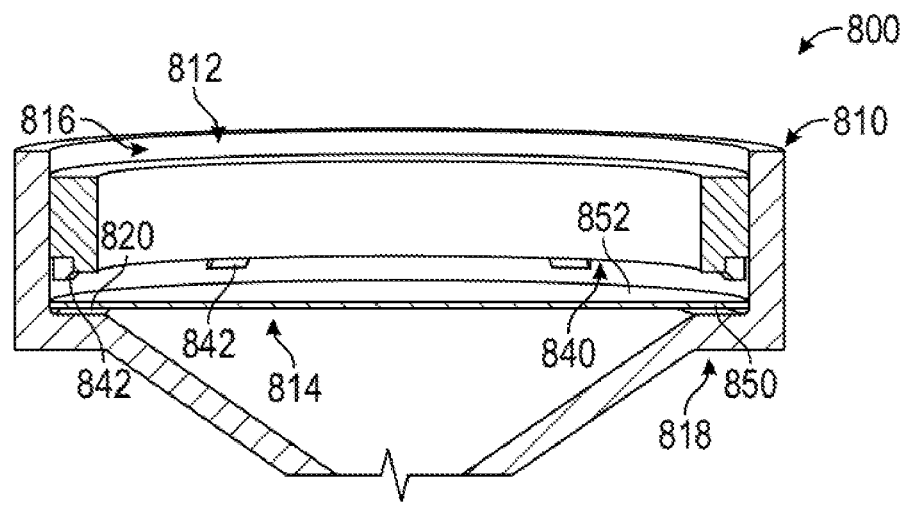
FIG. 8 is a perspective, exploded section view of a portion of a drip unit according to another embodiment, with an attachment component in the form of a washer different from that of FIGS. 6A through 7.

Referring to FIG. 8, a perspective, exploded section view illustrates a portion of a drip unit 800 according to another embodiment. The drip unit 800 may have a configuration similar to that of FIGS. 6A through 7. Thus, the drip unit 800 may have an exterior wall 810, an attachment component in the form of a washer 812, and an anti-run-dry membrane 814. The exterior wall 810 and the washer 812 may be secured together such that the anti-run-dry membrane 814 is sandwiched between them; thus, the anti-run-dry membrane 814 may be securely mechanically retained within a drip chamber 816 defined by the exterior wall 810. Since the washer 812 does not form a boundary of the drip chamber 816, a hermetic seal need not necessarily be formed between the washer 812 and the exterior wall 810.

As shown, the exterior wall 810 may have a generally tubular and/or frustoconical shape, with a shelf 818 with a generally annular shape. A seat 820 in the form of an annular surface may exist on the interior of the shelf 818. The membrane 814 may have a first attachment surface 850 facing toward the seat 820, and a second attachment surface 852 facing toward the washer 812. The washer 812 may have a generally annular shape, with an attachment surface in the form of a membrane-facing surface 840 having a plurality of anchoring elements 842 extending therefrom. Each of the anchoring elements 842 may lie along the interior surface of the exterior wall 810, adjacent to the seat 820. Each of the anchoring elements 842 may have a tapered shape configured to permit the anchoring elements 842 to puncture the anti-run-dry membrane 814 and/or deflect the outer edges of the anti-run-dry membrane 814 inward to permit motion of the anchoring elements 842 into contact with the seat 820.

As in the embodiment of FIGS. 6A through 7, the distal ends of the anchoring elements 842 may be butt welded, for example, via ultrasonic or laser welding, to the seat 820 of the exterior wall 810. Additionally or alternatively, the contact between the anchoring elements 842 and the interior surface of the exterior wall 810 may facilitate shear welding of the outward-facing edges of the anchoring elements 842 to the interior surface of the exterior wall 810. The drip unit 800 may be assembled in a manner similar to that of the drip unit 600 of FIGS. 6A through 7.

An attachment component within the scope of the present disclosure need not be a rigid structure. Rather, as used herein, an "attachment component" may be any cohesive structure with sufficient mechanical stiffness to mechanically retain an anti-run-dry membrane relative to an exterior wall. One exemplary attachment component with a more flexible structure will be shown and described in connection with FIG. 9, as follows.

Figure 9:
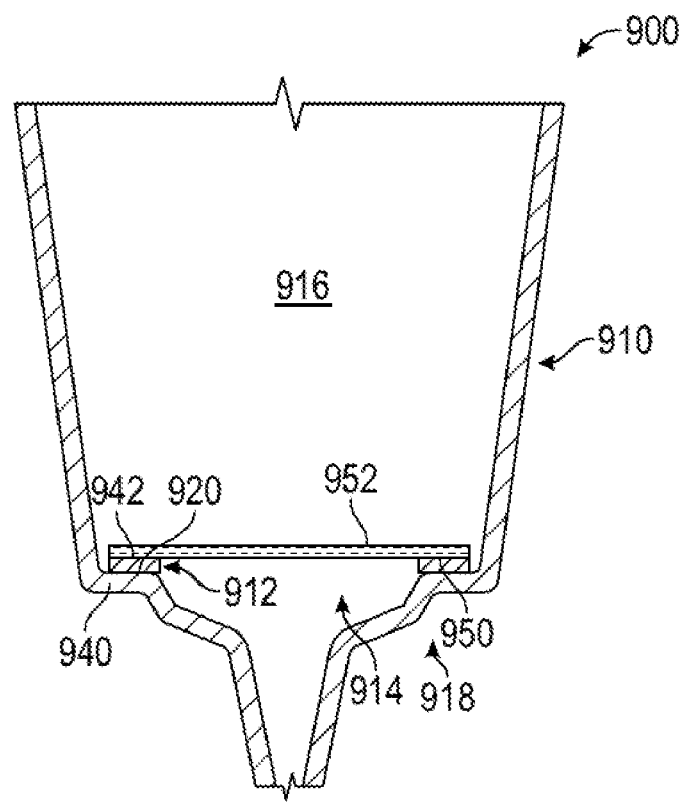
FIG. 9 is a front elevation, section view of a portion of a drip unit according to another embodiment, with an attachment component in the form of an adhesive ring.

Referring to FIG. 9, a front elevation, section view illustrates a portion of a drip unit 900 according to another embodiment. The drip unit 900 may have an exterior wall 910, an attachment component in the form of an adhesive ring 912, and an anti-run-dry membrane 914; thus, the anti-run-dry membrane 914 may be securely mechanically retained within a drip chamber 916 defined by the exterior wall 910.

As shown, the exterior wall 910 may have a generally tubular and/or frustoconical shape, with a shelf 918 with a generally annular shape. A seat 920 in the form of an annular surface may exist on the interior of the shelf 918. The membrane 914 may have a first attachment surface 950 facing toward the seat 920, and a second attachment surface 952 facing toward the adhesive ring 912. The adhesive ring 912 may have a generally annular shape, with a first attachment surface 940 facing toward the seat 920, and a second attachment surface 942 facing toward the anti-run-dry membrane 914.

The adhesive ring 912 may be formed of a pressure-sensitive adhesive. If desired, the adhesive ring 912 may be die cut and fed on a backer sheet, and then joined to the anti-run-dry membrane 914. More specifically, the second attachment surface 942 of the adhesive ring 912 may be placed in contact with the first attachment surface 950 of the anti-run-dry membrane 914. In response, the adhesive ring 912 may adhere to the first attachment surface 950 with a force sufficient to facilitate assembly.

Then, the adhesive ring 912 and the anti-run-dry membrane 914 may be placed on the seat 920 as illustrated in FIG. 9. The first attachment surface 940 of the adhesive ring 912 may adhere to the adhesive ring 912. Then, with the adhesive ring 912 and the anti-run-dry membrane 914 in place, the adhesive ring 912 may be compressed to cause the adhesive ring 912 to adhere more firmly to the seat 920 and the anti-run-dry membrane 914. This may be done, for example, by urging a fixture (not shown) into the drip chamber 916 and pressing the fixture against the second attachment surface 952 of the anti-run-dry membrane 914 to compress the adhesive ring 912 between the first attachment surface 950 of the anti-run-dry membrane 914 and the seat 920 of the exterior wall 910.

The adhesive ring 912 may form a structural bond and a hermetic seal between the anti-run-dry membrane 914 and the seat 920, thereby causing fluid to flow through the anti-run-dry membrane 914 in order to move from the upper portion of the drip chamber 916 into the lower portion of the drip chamber 916. If desired, other attachment methods may be applied in addition to the adhesion provided by the adhesive ring 912.

The embodiments shown and describe above represent only some examples of attachment components that may be used within the scope of the present disclosure. In some embodiments, one or more retention features may be used to facilitate and/or strength attachment of the anti-run-dry membrane to the exterior wall. In some embodiments, an interference fit may be provided between the anti-run-dry membrane and the exterior wall. Such an interference fit may help to mechanically retain the anti-run-dry membrane during the performance of other attachment and/or assembly steps, and may even provide more secure retention of the anti-run-dry membrane after assembly of the drip unit has been completed. Examples of retention features that use interference fits will be shown and described in connection with FIGS. 10 and 11, as follows.

Figure 10:
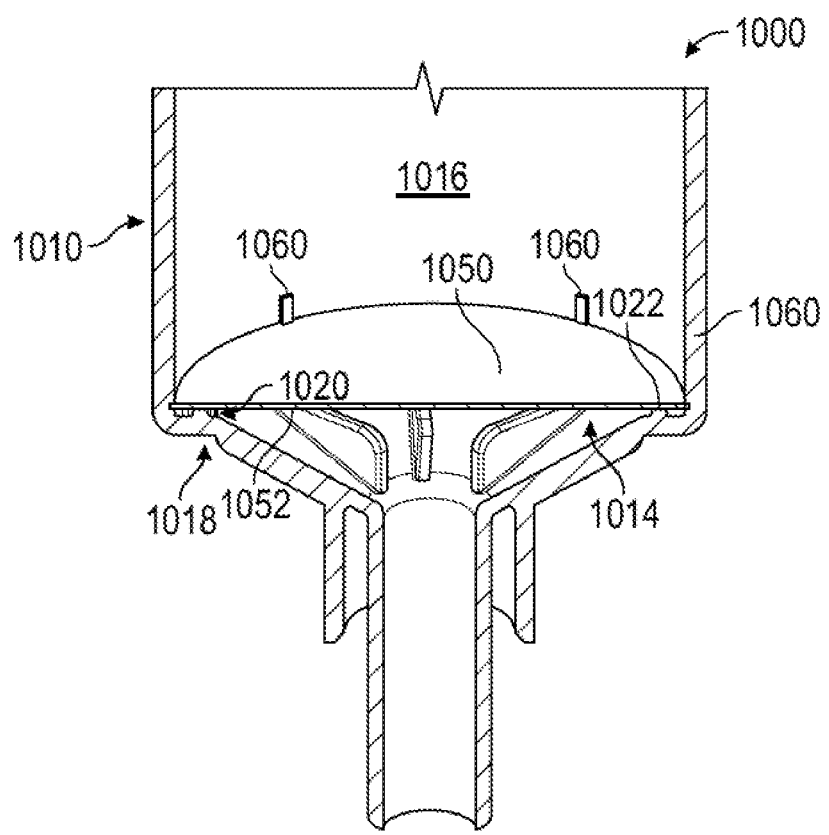
FIG. 10 is a perspective, section view of a portion of a drip unit according to another embodiment, with a plurality of interference features that protrude radially inward from an interior of the exterior wall to provide an interference fit with the anti-run-dry membrane.

Referring to FIG. 10, a perspective, section view illustrates a portion of a drip unit 1000 according to another embodiment. The drip unit 1000 may have an exterior wall 1010 and an anti-run-dry membrane 1014. The drip unit may also have an attachment component (not shown), which may be of any type disclosed herein.

As shown, the exterior wall 1010 may have a generally tubular and/or frustoconical shape, with a shelf 1018 with a generally annular shape. A seat 1020 in the form of an annular surface may exist on the interior of the shelf 1018. The membrane 1014 may have an attachment surface 1050 facing toward the seat 1020, and an opposing surface 1052 facing toward the upper portion of the drip chamber 1016. The seat 1020 may have a ridge 1022 on which the surface 1052 of the anti-run-dry membrane 1014 rests; the ridge 1022 may act as an energy director for a welding process such as ultrasonic welding.

The drip unit 1000 may have a plurality of retention mechanisms in the form of a plurality of interference features 1060 that protrude inward from the interior surface of the exterior wall 1010, proximate the seat 1020. The interference features 1060 may circumscribe a diameter slightly smaller than the diameter of the anti-run-dry membrane 1014. Thus, as the anti-run-dry membrane 1014 is moved into engagement with the seat 1020, the interference features 1060 may cause an interference fit to exist. This interference may be relatively small, for example, on the order of 0.001 inches to 0.004 inches. Thus, excessive deformation of the anti-run-dry membrane 1014 may be avoided.

The interference features 1060 may be relatively narrow flanges that, collectively, occupy only a relatively small portion of the circumference of the interior surface of the exterior wall 1010. This geometry may help to avoid the wrinkling or other more dramatic deformation of the anti-run-dry membrane 1014 that may otherwise occur if an interference fit exists around a larger portion of the circumference of the anti-run-dry membrane 1014. Rather, the relatively small width of the interference features may instead cause localized deformation to occur in the anti-run-dry membrane 1014 as the anti-run-dry membrane 1014 is urged into place on the seat 1020. However, the vast majority of the area of the anti-run-dry membrane 1014 may remain relatively undeformed.

The interference features 1060 may help keep the anti-run-dry membrane 1014 in place during the performance of other attachment features, such as ultrasonic welding of the attachment surface 1050 of the anti-run-dry membrane 1014 to the ridge 1022 of the seat 1020.

The interference features 1060 are merely exemplary. A wide variety of alternative interference feature configurations may be used within the scope of the present disclosure. Further, a wide variety of retention features that are not interference features may alternatively or additionally be used within the scope of the present disclosure. One alternative interference feature configuration will be shown and described in connection with FIG. 11.

Figure 11:
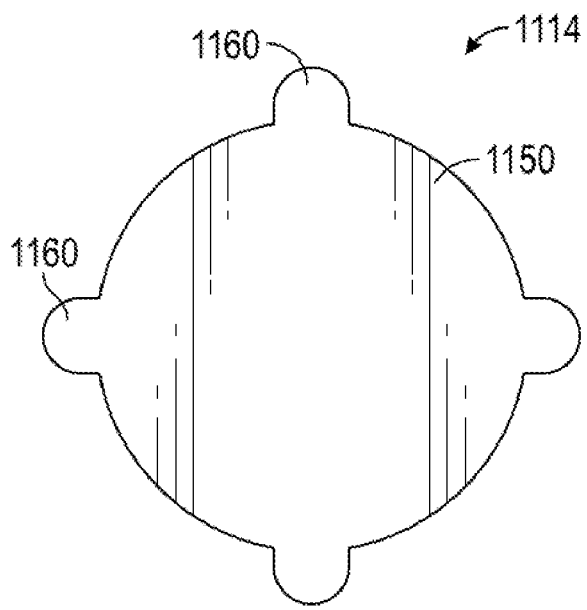
FIG. 11 is a plan view of an anti-run-dry membrane according to another embodiment, with a plurality of interference features that protrude radially outward from a periphery of the anti-run-dry membrane to provide an interference fit with an interior surface of an exterior wall.

Referring to FIG. 11, a plan view illustrates an anti-run-dry membrane 1114 according to another embodiment. The anti-run-dry membrane 1114 may be used in combination with any of the exterior walls disclosed in other embodiments, or with an exterior wall (not shown) with a different configuration. The anti-run-dry membrane 1114 may have an attachment surface 1150 that rests on a seat (not shown) of the exterior wall.

Further, the anti-run-dry membrane 1114 may have a plurality of retention features in the form of interference features 1160 that protrude outward, toward the interior surface of the exterior wall. The interference features 1160 may form an interference fit with the interior surface, for example, with interference ranging from 0.001 inches to 0.004 inches. During insertion of the anti-run-dry membrane 1114 into engagement with the seat of the exterior wall, the interference features 1160 may deflect (via bending, axial compression, or the like) to permit the insertion. The interference features 1160 may thus be loaded in stain, providing frictional engagement with the interior surface of the exterior wall. As in the embodiment of FIG. 10, the interference features 1160 may help keep the anti-run-dry membrane 1114 in place during and/or after the performance of other attachment and/or assembly steps, without causing excessive deformation of other parts of the anti-run-dry membrane 1114.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. An intravenous delivery system comprising:
   a drip unit comprising:
      an exterior wall shaped to at least partially define a drip chamber that receives a liquid from a liquid source, the exterior wall comprising a seat;
      an anti-run-dry membrane comprising a plurality of pores that are permeable to the liquid, wherein the anti-run-dry membrane is formed of a hydrophilic material configured to resist passage of air through the pores, the anti-run-dry membrane comprising an attachment surface; and an attachment component that secures the attachment surface to the exterior wall, proximate the seat, wherein the attachment component comprises a washer positioned such that the anti-run-dry membrane is between the washer and the seat, wherein the washer is secured to the exterior wall to hold the attachment surface in engagement with the seat.

2. The intravenous delivery system of claim 1, wherein the attachment component comprises the washer positioned such that the anti-run-dry membrane is between the washer and the seat, wherein the washer is secured to the exterior wall to hold the attachment surface in engagement with the seat.

3. The intravenous delivery system of claim 1, wherein the washer comprises a membrane facing surface with a plurality of anchoring elements that protrude through the anti-run-dry membrane, wherein each of the anchoring elements comprises a distal end butt welded to the seat.

4. The intravenous delivery system of claim 1, further comprising:

tubing comprising a first end connectable to the drip unit and a second end; and an intravenous access unit connectable to the second end of the tubing to deliver the liquid intravenously to a patient.

5. A method for manufacturing an intravenous delivery system, the method comprising:

providing a drip unit by:

providing an anti-run-dry membrane comprising a plurality of pores that are permeable to a liquid to be delivered to a patient, wherein the anti-run-dry membrane is formed of a hydrophilic material configured to resist passage of air through the pores, the anti-run-dry membrane comprising an attachment surface;

positioning an attachment component, wherein the attachment component comprises a washer, wherein positioning the attachment component comprises positioning the washer such that the anti-run-dry membrane is between the washer and the seat; and securing the attachment component to an exterior wall to keep the anti-run-dry membrane in place with the attachment surface abutting a seat of the exterior wall, wherein the exterior wall is shaped to at least partially define a drip chamber that receives the liquid from a liquid source.

6. The method of claim 5, wherein the washer comprises a membrane facing surface with a plurality of anchoring elements;

wherein positioning the washer such that the anti-run-dry membrane is between the washer and the seat comprises causing the anchoring elements to protrude through the anti-run-dry membrane;

wherein securing the washer to the exterior wall comprises butt welding a distal end of each of the anchoring elements to the seat.

7. The method of claim 5, further comprising:

providing tubing comprising a first end connectable to the drip unit and a second end; and providing an intravenous access unit connectable to the second end of the tubing to deliver the liquid intravenously to a patient.

* * * * *